United States Patent
Shen et al.

[19]

[11] Patent Number: 6,080,294
[45] Date of Patent: Jun. 27, 2000

[54] GAS SENSOR WITH DUAL ELECTROLYTES

[75] Inventors: Yousheng Shen, Salt Lake City; Franco Consadori, West Valley City, both of Utah

[73] Assignee: Atwood Industries, Inc., Rochester Hills, Mich.

[21] Appl. No.: 09/116,121

[22] Filed: Jul. 15, 1998

[51] Int. Cl.[7] .................................................. G01N 27/404
[52] U.S. Cl. ........................ 204/415; 204/421; 204/424
[58] Field of Search ............................. 204/421–429, 204/415, 431, 432

[56] References Cited

U.S. PATENT DOCUMENTS

| | | | |
|---|---|---|---|
| 2,861,926 | 11/1958 | Jacobson | 204/432 |
| 2,913,386 | 11/1959 | Clark | 204/415 |
| 3,668,101 | 6/1972 | Bergman | 204/415 |
| 3,776,831 | 12/1973 | Roy et al. | 204/422 |
| 4,296,752 | 10/1981 | Welsh et al. . | |
| 4,323,440 | 4/1982 | Akatsuka . | |
| 4,324,632 | 4/1982 | Tantram et al. . | |
| 4,347,114 | 8/1982 | Kimura et al. . | |
| 4,450,065 | 5/1984 | Yamada et al. . | |
| 4,466,879 | 8/1984 | Ho et al. . | |
| 4,495,051 | 1/1985 | Fujita et al. . | |
| 4,533,456 | 8/1985 | Kratochvil et al. . | |
| 4,547,281 | 10/1985 | Wang et al. . | |
| 4,672,971 | 6/1987 | Otten . | |
| 4,695,361 | 9/1987 | Grady . | |
| 4,775,456 | 10/1988 | Shah et al. . | |
| 4,784,743 | 11/1988 | Iino et al. . | |
| 4,789,454 | 12/1988 | Badwal et al. . | |
| 4,815,469 | 3/1989 | Cohen et al. . | |
| 4,861,454 | 8/1989 | Ushizawa et al. . | |
| 4,861,727 | 8/1989 | Hauenstein et al. . | |
| 4,950,380 | 8/1990 | Kurosawa et al. . | |
| 5,024,226 | 6/1991 | Tan . | |
| 5,071,626 | 12/1991 | Tuller . | |
| 5,102,525 | 4/1992 | Miyahara et al. . | |
| 5,106,482 | 4/1992 | Milstein et al. . | |
| 5,113,862 | 5/1992 | Mortazavi . | |
| 5,141,607 | 8/1992 | Swiat | 205/734 |
| 5,178,744 | 1/1993 | Nakazawa et al. . | |
| 5,271,816 | 12/1993 | Tanaka et al. . | |
| 5,284,566 | 2/1994 | Cuomo et al. . | |
| 5,302,274 | 4/1994 | Tomantschger et al. | 204/415 |
| 5,342,406 | 8/1994 | Thompson . | |
| 5,346,605 | 9/1994 | Wolcott et al. | 204/415 |
| 5,401,376 | 3/1995 | Foos et al. | 204/415 |
| 5,573,648 | 11/1996 | Shen et al. . | |
| 5,650,054 | 7/1997 | Shen et al. . | |

OTHER PUBLICATIONS

Nei, Lembit et al, *An Improved Clark–type Galvanic Sensor for Dissolved Oxygen*, pp. 83–87, Elsevier Science S.A., 1996 month unavailable.

Zaluski, C.S. et al, *AC Impedance and Conductivity Study of Alkali Salt Form Perfluorosulfonate Ionomer Membranes*, vol. 141, pp. 448–451, J. Electrochem Soc., 1994 month unavailable.

*Primary Examiner*—T. Tung
*Attorney, Agent, or Firm*—Banner & Witcoff, Ltd.

[57] ABSTRACT

A highly accurate, long life, low cost gas sensor is disclosed, particularly useful for measuring oxygen in an environment. The gas sensor has a first, sensing electrode and a second, counting electrode. Dual electrolytes are electrically serially connected between the first and second electrodes. One of the electrolytes is an ion conducting solid electrolyte, the second is a liquid electrolyte. In response to an electric current an electrical characteristic is produced, and the electrical characteristic changes in response to changes in the concentration of a gas such as oxygen introduced at the first, sensing electrode. The solid electrolyte can be a perfluorinated polymer which advantageously controls the rate of the electrochemical reaction to give the sensor a long life without need for continuous recalibration. A dense liquid impermeable membrane may be positioned over the first electrode so that only gas reaches the first electrode and all gas that reaches the first electrode passes through the membrane. Advantageously, the solid electrolyte isolates the liquid electrolyte from the first, sensing electrode. The liquid electrolyte may comprise an acidic solution, a basic solution or a salt solution.

30 Claims, 2 Drawing Sheets

# GAS SENSOR WITH DUAL ELECTROLYTES

FIELD OF THE INVENTION

The present invention generally relates to gas sensors, and more particular to improved gas sensors for detecting oxygen.

BACKGROUND OF THE INVENTION

Gas sensors for sensing oxygen are used in a wide variety of applications where the amount of oxygen must be measured. Examples of uses for such oxygen sensors include use in fuel-air mixtures and exhaust systems in combustion engines, gas burning appliances, for use in measurement of oxygen levels in blood and in regulation of anesthesia, and environmental applications. One known technique for measuring oxygen is a ceramic based sensor. Ceramic base sensors are commonly used in the automobile industry for combustion exhaust monitoring. Examples of ceramic based oxygen sensors include U.S. Pat. Nos. 4,547,281 to Wang et al, or 4,950,380 to Kurosawa et al. These types of ceramic sensors are disadvantageous in that they require operating temperatures approaching 400° C. to be effective, which may make it inappropriate for certain applications. It would be desirable to have an accurate oxygen sensor having both good stability characteristics and be operable at temperatures significantly below 400° C.

Another known technique for measuring oxygen in an external environment is a galvanic cell type oxygen sensor, where typically a liquid electrolyte, often an acid in an aqueous solution, is positioned between positive and negative electrodes (a cathode and an anode) and a current is passed between the electrodes. Oxygen is presented to the cathode. An oxidation reaction occurs at the anode and a reduction reaction occurs at the cathode. The potential difference between the electrodes is proportional to the concentration of oxygen sensed at the cathode. Such sensors are capable of measuring oxygen concentrations near room temperature, commonly in medical and environmentally applications. Examples of such galvanic cell or liquid electrolyte oxygen sensors include, for example, U.S. Pat. Nos. 4,495,051 to Fujita et al, 4,775,456 to Shah et al, 4,988,428 to Matthiessen et al, and 5,284,566 to Cuomo et al.

Although such liquid electrolyte oxygen sensors work at ambient temperatures, such sensors have numerous problems. The chemical reaction of the liquid electrolyte tends to run fairly quickly, limiting the total operational lifespan of such oxygen sensors. Moreover, the rate of reaction, which affects potential difference between the electrodes, is a function of the concentration of the liquid electrolyte, and the concentration of electrolyte changes as the reaction runs. Further, the concentration of liquid electrolyte changes as it dries out over its service life. This means that such oxygen sensors need to be regularly recalibrated, often on a daily basis, to account for the change in concentration of the electrolyte. Compensation for such problems drives up the cost of the sensor and reduces their effectiveness. It would be highly desirable to provide an oxygen sensor which would last for an extended period of time and not require continuous recalibration.

In view of the foregoing, it is an object of the present invention to provide a gas sensor for sensing oxygen having a long operational lifespan which is highly reliable in operation and does not need to be recalibrated after initial setting. It is an additional object of the present invention to provide an oxygen sensor for use in an oxygen detector having fast response times. It is an additional object of the present invention to provide an oxygen sensor which is of low cost, compact size and is easy to manufacture.

SUMMARY OF THE INVENTION

There is provided a low cost sensor for sensing gas, especially oxygen, which has a first electrode and a second electrode with one or more electrolytes operatively connected between the electrodes. Preferably one of the electrolytes is a solid and one is a liquid. The solid electrolyte can conduct either cations or anions. In response to an electric current passed through the sensor, an electrical characteristic is generated between the first electrode and the second electrode. The electrical characteristic, which can be for example, potential difference, difference in current or impedance can be measured by a voltmeter. The electrical characteristic changes with the concentration of gas presented to the first electrode. According to one embodiment of the present invention, the solid electrolyte controls the rate of reaction when the solid electrolyte has a resistivity much greater than the liquid electrolyte. This higher resistivity advantageously greatly increases the operational life of the sensor, while still permitting rapid response time and accurate measurement.

The liquid electrolyte can comprise an aqueous solution of either an acid, a base or a salt. As the solid electrolyte is the principal control in the rate of reaction, additional materials may be added to the liquid electrolyte to increase the amount of ions in the liquid electrolyte and thereby facilitate higher rates of reaction.

In accordance with an additional embodiment of the present invention, an oxygen sensor is provided with a liquid impermeable membrane positioned between the oxygen to be sensed and a cathode. The membrane is capable of allowing oxygen to pass through the membrane. A solid electrolyte conducts ions between a top surface and a bottom surface of the solid electrolyte in response to an electric current. The ions are conducted through the solid electrolyte to react with oxygen in a reduction reaction at or near the top surface of the solid electrolyte. A liquid electrolyte is electrically connected to the solid electrolyte. Positioned in contact with the liquid electrolyte is an anode. In response to the electric current the anode is oxidized in an oxidation reaction and ions are released to the solid electrolyte.

In accordance with a third aspect, an oxygen sensor is provided with a solid electrolyte which is exposed to the oxygen to be sensed and is capable of conducting ions, a liquid electrolyte in serial electrical connection with the solid electrolyte, and a cathode in contact with the solid electrolyte and physically isolated from the liquid electrolyte. In response to an electric current, ions pass through the solid electrolyte and react with oxygen in a reduction reaction at or near the cathode. An oxidation reaction occurs at or near an anode positioned in contact with a liquid electrolyte.

From the foregoing disclosure and the following more detailed description of various preferred embodiments it will be apparent to those skilled in the art that the present invention provides a significant advance in the technology and art of gas sensors which sense oxygen. Particularly significant in this regard is the potential the invention affords for providing an oxygen sensor of low cost, compact size and long life without the need for additional elements to allow for recalibration. Additional features and advantages of various preferred embodiments will be better understood in view of the detailed description provided below.

Figure 1:
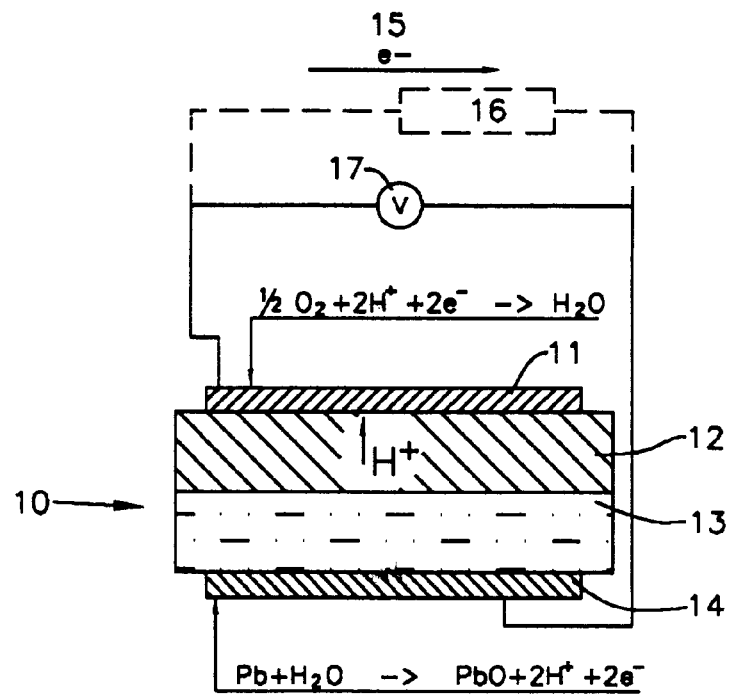
FIG. 1 is a simplified schematic of a preferred embodiment of a potentiometric oxygen sensor in accordance with the present invention wherein the liquid electrolyte is an aqueous solution comprising at least in part an acid, showing the transport process wherein hydrogen ions conducted across the solid electrolyte to the cathode in response to an electric current.

It should be understood that the appended drawings are not necessarily to scale, presenting a somewhat simplified representation of various preferred features illustrative of the basic principles of the invention. The specific design features of the oxygen sensors disclosed here, including, for example, the cross sectional thickness of the solid electrolyte membrane, and the specific composition of the liquid electrolyte will be determined in part by the particular intended application and use environment. Certain features of the illustrated embodiments have been enlarged or distorted relative to others to facilitate visualization and clear understanding. In particular, thin features (such as the cathode) may be thickened for clarity of illustration. All references to direction and position, unless otherwise indicated, refer to the orientation of the oxygen sensor illustrated in the drawings. In general, lateral or laterally refers to a rightward or leftward direction in the plane of the paper in FIG. 3, and top, bottom, or vertical refers to corresponding directions in the plane of the paper in FIG. 3. The same reference numerals are used in the drawings to identify identical features of different preferred embodiments.

DETAILED DESCRIPTION OF CERTAIN PREFERRED EMBODIMENTS

It will be apparent to those skilled in the art, that is, to those who have knowledge or experience in this area of technology, that many design variations are possible for the oxygen sensors disclosed herein. The following detailed discussion of various alternative and preferred features and embodiments will illustrate the general principles of the invention with reference to a gas sensor suitable for measuring oxygen and used in an oxygen detector in a gas appliance such as a furnace or a hot water heater. Other embodiments suitable for other applications will be apparent given the benefit of this disclosure.

Referring now to the drawings, FIG. 1 shows the transport process for one preferred embodiment of a dual electrolyte gas sensor 10 having fast response time and long life. Gas sensor 10 is particularly suited for measuring oxygen, and has cathode 11 and anode 14. Dual electrolytes, 12, 13 are operatively positioned in relation to the cathode 11 and anode 14, preferably so that they are electrically serially connected with one another as indicated in FIG. 1. Preferably the first electrolyte is a solid electrolyte 12 and the second electrolyte is a liquid electrolyte 13. Cathode 11 and anode 14 are electrically connected through an external resistor 16, closing the circuit and thereby allowing electrons to be transported from the cathode to the anode. Oxygen contacts or is otherwise introduced to the cathode 11, and in response to direct electric current 15 a reduction reaction takes place at the cathode 11, and an oxidation reaction takes place at the anode as represented below:

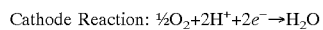

Cathode Reaction: $\frac{1}{2}O_2 + 2H^+ + 2e^- \rightarrow H_2O$

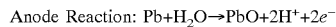

Anode Reaction: $Pb + H_2O \rightarrow PbO + 2H^+ + 2e^-$

The above equations apply where the anode 14 is lead (Pb) and the liquid electrolyte 13 comprises an aqueous acidic solution. In response to an electric current the lead anode 14 reacts with water to generate hydrogen ions (protons) and electrons. As seen in FIG. 1, hydrogen ions migrate across the solid electrolyte 12 to the cathode 11 where they react with oxygen to produce water. As discussed in greater detail below, the rate of this electrochemical reaction is generally proportional only to the amount of oxygen in the environment to be sensed. In addition, the potential difference between the cathode 11 and the anode 14 is generally proportional to the rate of the electrochemical reaction. A voltmeter 17 may be used to measure this potential difference, or voltage drop across the electrolytes, thereby enabling electric measurement of the amount of oxygen in the environment. Other suitable devices for measuring changes in the electric signal or characteristic (such as changes in current or impedance, etc.) between the cathode 11 and the anode 14 will be readily apparent to those skilled in the art given the benefit of this disclosure.

Figure 2:
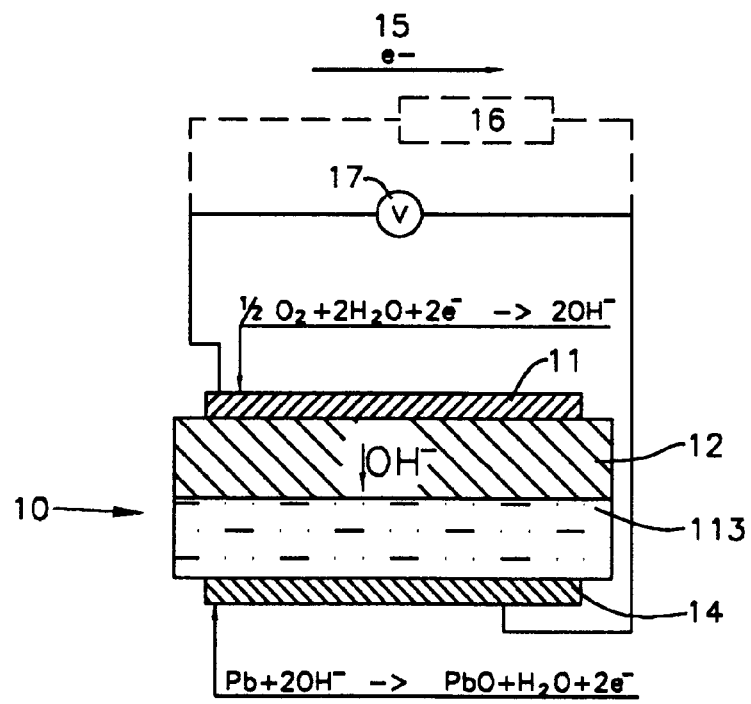
FIG. 2 is a simplified schematic of an alternative preferred embodiment of a potentiometric oxygen sensor wherein the liquid electrolyte is an aqueous solution of at least in part a base or a salt, and hydroxyl groups are transported across the solid electrolyte to the cathode in response to an electric current.

FIG. 2 shows an alternative preferred embodiment of an oxygen sensor 110 where the cathode 11 and anode 14 are the same, and the solid electrolyte 12 is the same, but the liquid electrolyte 113 now comprises either an aqueous solution of a base or a salt, or a combination of a base and a salt. The reactions at the cathode 11 and the anode 14 in response to a direct electric current when oxygen is sensed at the cathode are:

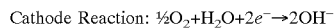

Cathode Reaction: $\frac{1}{2}O_2 + H_2O + 2e^- \rightarrow 2OH^-$

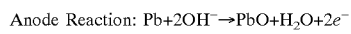

Anode Reaction: $Pb + 2OH^- \rightarrow PbO + H_2O + 2e^-$

In this embodiment, the transport process has hydroxyl groups (OH⁻) migrating across the solid electrolyte 12 as electrons flow from the cathode to the anode. According to the teachings of the present invention, irrespective of whether the liquid electrolyte comprises an acidic solution, a basic solution, or a salt solution, when the cathode is exposed to oxygen and a current is supplied, a reduction reaction takes place at the cathode and an oxidation reaction occurs at the anode.

Figure 3:
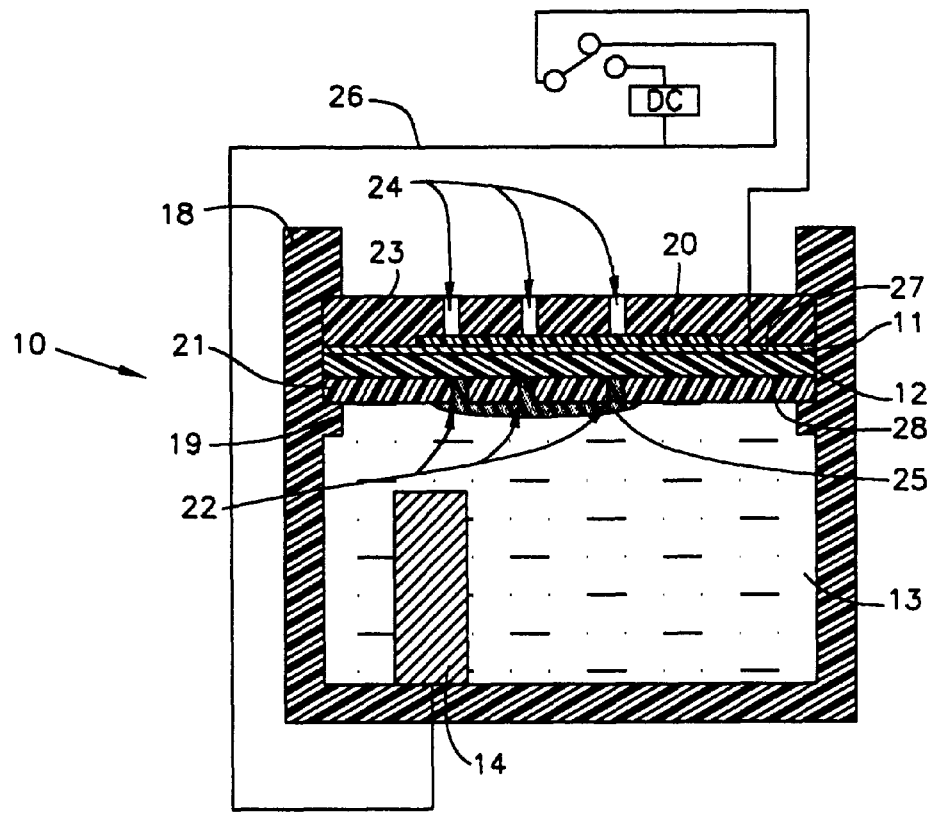
FIG. 3 is a cross section view of a preferred embodiment of an oxygen sensor, shown positioned in a housing and sealed from the environment by a liquid impermeable, oxygen permeable membrane.

FIG. 3 shows a cross section view of a preferred embodiment of an oxygen sensor 10, somewhat simplified for clarity of illustration. Oxygen sensor 10 has a housing 18 preferably made of plastic or some other non-conductive, non-reactive material, and is further provided with top spacer or cap 23. Top spacer 23 forms an airtight and watertight seal such that elements from the environment can only penetrate into the sensor through openings 24. A liquid impermeable and oxygen permeable polymer membrane 20 is positioned adjacent the openings 24, preventing access by any external liquids to the electrolytes 12 and 13. Preferably the polymer membrane 20 is a dense membrane comprising a polymer such as polytetrafluoroethylene (PTFE), having a thickness of approximately 20 micrometers, impermeable to water vapor and permeable to oxygen. Preferably the membrane 20 is positioned so that all oxygen from the environment passes through it on the way to the cathode 11.

A bottom spacer 21 is positioned on ledge 19 of housing 18. Bottom spacer 21 acts as a mount to receive the bottom surface of solid electrolyte 12. Cathode 11 may be applied as a coating to a top surface of the solid electrolyte 12 and formed of a thin film of conductive material such as a metal, most preferably gold, platinum, palladium or the like. Where gold is used, the film cathode 11 may have a thickness of approximately 1 micrometer, which allows the cathode 11 to be sufficiently porous to allow oxygen from the environment to pass through to the top surface of the solid electrolyte 12 while maintaining electrical conductivity. The reduction reaction takes place at or near a boundary between the cathode 11 and the solid electrolyte 12. The solid electrolyte 12 is a membrane which allows ions to pass from a bottom surface 28 to a top surface 27 where they react with oxygen in the reduction reaction described above. Conductor 26 completes the electron flow path by either directly contacting the electrode 11 as shown in FIG. 1 or by contacting another conducting element (such as the top cap) which itself is in electrical contact with electrode 11 in a manner readily apparent to those skilled in the art given the benefit of this disclosure.

The solid electrolyte 12 preferably comprises a thin membrane of a perfluorosulfonate ionomer such as those supplied by DUPONT under the trademark NAFION 117, PALL RAI's R4010 membrane or those supplied by DOW under the trademark XUS-1304. NAFION membranes incorporate (PTFE) like backbones with perfluorocarbon sulfonate sidechains to facilitate ion transport across the membrane. NAFION membranes have a preferred thickness in the range of approximately 0.05 to 1 mm, although NAFION membranes with smaller thicknesses could be used if they are commercially available. The XUS membranes are similar with PTFE like backbones but contain much shorter sidechains of the form [—O—$CF_2$—$CF_2$—$SO_3^-$]. Examples of solid electrolytes can be found in PROTON CONDUCTORS, SOLID, MEMBRANES AND GELS—MATERIALS AND DEVICES, edited by Philippe Colomban, Cambrige University Press, 1992. Other suitable materials for use as an ion conducting solid electrolyte 12 will be readily apparent to those skilled in the art given the benefit of this disclosure.

Looking in greater detail at the relationship between the voltage drop between the electrodes 11, 14 and the oxygen concentration in the environment, the voltage drop changes with both the oxygen concentration in the environment and the change in resistance between the electrodes. In order to ensure repeatable, accurate measurement of oxygen in the environment, changes in resistance between the electrodes must be minimized. Such resistance is caused by inherent electrolyte resistance, interface resistance between the electrodes and the electrolytes, and electrode resistance. In known designs when a current is supplied and the reaction proceeds, the resistivity of the liquid electrolyte changes with time as the amount of ions available for transport to the cathode steadily decreases. Furthermore, in known designs where an acidic solution is used in the liquid electrolyte, the acid interacts with the cathode to deleteriously affect the resistance of the electrodes. For these reasons, existing liquid electrolyte based oxygen sensors cannot adequately account for changes in this resistivity with time. To compensate, continuous recalibration of known oxygen sensors is required.

Advantageously, use of a solid electrolyte 12 in the present invention, minimizes changes in resistance so that potential difference between the electrodes changes largely only in response to the partial pressure of oxygen presented at the cathode. Change in total resistance between the electrodes is negligible for many years, even as the resistance of the liquid electrolyte changes. This is achieved because solid electrolytes, with resistance levels typically an order of magnitude greater than the resistance of liquid electrolytes, greatly reduce the overall rate of the electrochemical reaction in the oxygen sensor. Moreover, use of a solid electrolyte 12 allows the cathode 11 to be physically isolated from the liquid electrolyte 13, thereby greatly reducing changes in resistance of the cathode due to corrosive attack from the acid in the liquid electrolyte.

The liquid electrolyte 13 may comprise an acidic solution, a basic solution, or a salt solution, most preferably an acidic solution with 5.5 mol concentration acetic acid ($CH_3COOH$), 4.5 mol sodium acetate ($CH_3COONa$), and 0.2 mol lead acetate ($CH_3CO_2)_2Pb \cdot 3H_2O$. The compounds added to the acid increase the ions in solution to facilitate the reaction. For liquid electrolytes where a basic solution is used, the base can be, for example, potassium hydroxide (KOH). Salts which are highly acidic or highly basic in solution (that is, salts that have pH levels higher than or less than 7) may also be used. One example of a salt which is highly acidic in solution is calcium sulfate ($CaSO_4$). One example of a salt which is highly basic in solution is potassium carbonate ($K_2CO_3$). Salts may also be added with an acid or a base to increase the number of ions in solution. When the liquid electrolyte 13 is an acidic solution, hydrogen ions, $H^+$ are transported across the solid electrolyte 12 to the cathode 11. When the liquid electrolyte 113 is a basic solution, hydroxyl ions, ($OH^-$) are transported across the solid electrolyte. Other suitable liquid electrolyte solutions in accordance with this invention will be apparent to those skilled in the art given the benefit of this disclosure.

In FIG. 3 a sponge 25 extending into openings 22 in bottom spacer 21 is used as one technique to ensure complete contact between the liquid and solid electrolytes. Anode 14 may be lead, or another metal such as cadmium.

Figure 4:
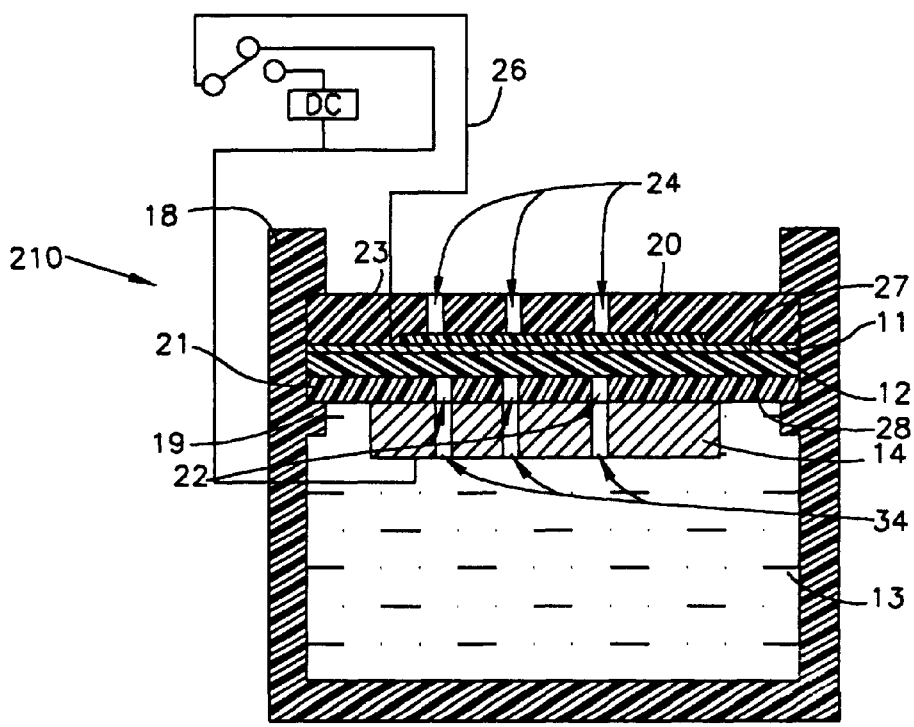
FIG. 4 is a cross section view of an alternative preferred embodiment showing an anode positioned in the liquid electrolyte generally adjacent the solid electrolyte.

FIG. 4 shows an alternative preferred embodiment of an oxygen sensor 210 where the anode 14 is positioned generally adjacent the bottom spacer 21, and is provided with openings 34 generally aligned with openings 22 in the bottom space to permit access by the liquid electrolyte 13 to the solid electrolyte 12, thereby completing the electrical connection.

From the foregoing disclosure and detailed description of certain preferred embodiments, it will be apparent that various modifications, additions and other alternative embodiments are possible without departing from the true scope and spirit of the invention. For example, oxygen sensors of this type can find ready application in food packaging or in medical devices where it is important to monitor oxygen levels, such as anesthesia equipment. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A gas sensor for measurement of a gas in an environment comprising, in combination:

a first electrode;

a membrane permeable to the gas and impermeable to water vapor, positioned between the environment and the first electrode;

a second electrode;

a solid electrolyte positioned between the first electrode and the second electrode;

a liquid electrolyte isolated from the gas to be measured, positioned between the first electrode and the second electrode, electrically serially connected to the solid electrolyte, and cooperating with the solid electrolyte in response to an electric current to produce a voltage between the first electrode and the second electrode, wherein the voltage changes in response to changes in the concentration of the gas wherein the second electrode is in direct contact with the liquid electrolyte; and means for electrical measurement of the voltage electrically connected to the first electrode and the second electrode.

2. The gas sensor of claim 1 wherein the solid electrolyte is a cationic conductive membrane, substantially composed of a solid, perfluorinated polymer.

3. The gas sensor of claim 1 wherein the first electrode is a metal coating applied to a surface of the solid electrolyte.

4. The gas sensor of claim 1 wherein the first electrode comprises a metal selected from the group of gold, platinum and palladium.

5. The gas sensor of claim 1 wherein the means for electrical measurement comprises a voltage meter which measures potential difference between the first electrode and the second electrode.

6. The gas sensor of claim 1 wherein the liquid electrolyte comprises an aqueous solution of an organic acid.

7. The gas sensor of claim 6 wherein the organic acid is acetic acid, the liquid electrolyte further comprises an aqueous solution of sodium acetate and lead acetate, and the solid electrolyte conducts hydrogen ions to the first electrode.

8. The gas sensor of claim 1 wherein the liquid electrolyte comprises an aqueous solution of a salt.

9. The gas sensor of claim 8 wherein the salt is sodium chloride and the solid electrolyte conducts hydroxyl ions to the first electrode.

10. The gas sensor of claim 1 wherein the liquid electrolyte comprises an aqueous solution of a base.

11. The gas sensor of claim 10 wherein the base is potassium hydroxide and the solid electrolyte conducts hydroxyl ions to the first electrode.

12. The gas sensor of claim 1 further comprising a gas permeable, liquid impermeable solid polymer membrane positioned between the solid electrolyte and the environment so that only gas from the environment penetrates the membrane to reach the solid electrolyte.

13. The gas sensor of claim 12 wherein the solid polymer membrane comprises a dense polytetrafluoroethlyene film.

14. The gas sensor of claim 1 wherein the second electrode comprises lead and is positioned in electrical contact with the liquid electrolyte.

15. The gas sensor of claim 1 further comprising:

a housing for receiving the liquid electrolyte and the solid electrolyte;

a top cover and a bottom spacer, wherein the top cover is positioned between the environment and the solid electrolyte, and the bottom spacer is positioned between the solid electrolyte and the liquid electrolyte.

16. The gas sensor of claim 15 wherein the bottom spacer is positioned on a ledge extending from the housing and supports the solid electrolyte, and the bottom spacer has a plurality of openings which permit the liquid electrolyte to contact the solid electrolyte.

17. The gas sensor of claim 1 wherein a reduction reaction occurs at the first electrode and an oxidation reaction occurs at the second electrode.

18. An oxygen sensor comprising, in combination:

a solid polymer membrane permeable to oxygen and impermeable to water vapor;

a solid polymer electrolyte having a top surface and a bottom surface and being capable of conducting ions between the top surface and the bottom surface;

a liquid electrolyte isolated from the gas to be measured, electrically connected to the solid polymer electrolyte;

a metal in direct contact with the liquid electrolyte, wherein in response to electrical current the metal is oxidized in an oxidation reaction; and an electrically conductive metal film in electrical connection with the top surface of the solid polymer electrolyte and separated from the liquid electrolyte by the solid electrolyte;

wherein oxygen passes through the polymer membrane, and in response to an electric current ions are conducted through the solid polymer electrolyte to react with the oxygen in a reduction reaction near the top surface of the solid polymer electrolyte.

19. The oxygen sensor of claim 18 wherein the metal is selected from the group consisting of lead and cadmium.

20. The oxygen sensor of claim 18 further comprising a spacer having a plurality of openings allowing the liquid electrolyte to contact the solid electrolyte, wherein the metal is positioned adjacent the spacer.

21. The oxygen sensor of claim 18 wherein the solid polymer membrane comprises dense polytetrafluoroethylene, the solid electrolyte comprises a thin membrane of a perfluorosulfonate ionomer, and the electrically conductive metal film is gold.

22. A sensor for sensing oxygen in an environment comprising, in combination:

a first electrode;

a polymer membrane permeable to oxygen and impermeable to water vapor, positioned between the environment and the first electrode;

a second electrode, wherein in response to an electric current a voltage is produced between the first electrode and the second electrode which is proportional to the concentration of oxygen sensed at the first electrode;

a first electrolyte and a second electrolyte, wherein the first electrolyte is in direct contact with the second electrolyte such that the first electrolyte isolates the first electrode from the second electrolyte, and the second electrolyte is isolated from the oxygen to be sensed and the second electrode is in direct contact with the second electrolyte.

23. The sensor of claim 22 wherein in response to an electric current the oxygen reacts in a reduction reaction at the first electrode.

24. The sensor of claim 23 wherein the first electrolyte is a solid electrolyte capable of conducting ions, and the ions react with oxygen in the reduction reaction.

25. The sensor of claim 24 wherein the ions are hydrogen ions and the second electrolyte is a liquid electrolyte comprising an aqueous solution of an organic acid.

26. The sensor of claim 24 wherein the ions are hydroxyl ions and the second electrolyte is a liquid electrolyte comprising an aqueous solution of one of a base and a salt.

27. The sensor of claim 23 wherein the rate of the reduction reaction at the first electrode is proportional to the concentration of oxygen sensed at the first electrode.

28. The sensor of claim 22 wherein an oxidation reaction occurs near a boundary between the second electrode and the second electrolyte generating electrons.

29. The sensor of claim 28 wherein the second electrode is an anode comprising lead which in the oxidation reaction is oxidized to form lead oxide.

30. The oxygen sensor of claim 22 wherein the second electrolyte is a liquid electrolyte and further comprising a sponge positioned in the liquid electrolyte, in contact with the first electrolyte.

* * * * *